(12) United States Patent
Kim et al.

(10) Patent No.: US 11,624,686 B2
(45) Date of Patent: Apr. 11, 2023

(54) METHOD FOR DETERMINING CONCENTRATED FORM OF ANALYTE AND METHOD FOR CONVERTING CONCENTRATED FORM OF ANALYTE

(71) Applicant: SEOUL NATIONAL UNIVERSITY R&DB FOUNDATION, Seoul (KR)

(72) Inventors: Sung Jae Kim, Seoul (KR); Hyomin Lee, Incheon (KR); Jihye Choi, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 933 days.

(21) Appl. No.: 16/467,532

(22) PCT Filed: Jan. 12, 2018

(86) PCT No.: PCT/KR2018/000579
§ 371 (c)(1),
(2) Date: Jun. 7, 2019

(87) PCT Pub. No.: WO2018/135808
PCT Pub. Date: Jul. 26, 2018

(65) Prior Publication Data
US 2019/0323930 A1    Oct. 24, 2019

(30) Foreign Application Priority Data
Jan. 23, 2017    (KR) .......................... 10-2017-0010641

(51) Int. Cl.
*G01N 1/40*    (2006.01)
*G01N 33/483*    (2006.01)
(Continued)

(52) U.S. Cl.
CPC ................ *G01N 1/40* (2013.01); *C12Q 1/02* (2013.01); *G01N 27/44795* (2013.01);
(Continued)

(58) Field of Classification Search
CPC .................. G01N 1/40; G01N 33/483; G01N 2001/4038; G01N 27/44795; C12Q 1/02;
(Continued)

(56) References Cited

U.S. PATENT DOCUMENTS

| 2009/0242406 A1* | 10/2009 | Han | ................. | B01L 3/502707 204/520 |
| 2011/0220498 A1* | 9/2011 | Ko | ................... | G01N 27/44791 137/833 |
| 2022/0111386 A1* | 4/2022 | Anand | .............. | B01L 3/502792 |

FOREIGN PATENT DOCUMENTS

| JP | 2003270227 A | 9/2003 |
| JP | 2016075537 A | 5/2016 |

(Continued)

OTHER PUBLICATIONS

Jia et al. Analytical Chemistry, vol. 86, Jul. 17, 2014, pp. 7360-7367.*

(Continued)

*Primary Examiner* — Maureen Wallenhorst
(74) *Attorney, Agent, or Firm* — Stuart H. Mayer; Mayer & Williams PC

(57) ABSTRACT

Provided are a method of determining a preconcentration type of an analyte and a method of converting a preconcentration type of an analyte. A method of determining a preconcentration type of an analyte, according to an embodiment of the present invention, includes (a) establishing a critical mobility model, (b) calculating a critical mobility by applying a parameter value to the critical mobility model, and (c) determining the preconcentration type of the analyte by comparing the calculated critical mobility to an absolute value of an electrophoretic mobility of the analyte.

14 Claims, 5 Drawing Sheets

(51) Int. Cl.
*G01N 27/447* (2006.01)
*G01R 31/00* (2006.01)
*G06F 30/20* (2020.01)
*C12Q 1/02* (2006.01)
*G06F 111/10* (2020.01)

(52) U.S. Cl.
CPC .......... *G01N 33/483* (2013.01); *G01R 31/00* (2013.01); *G06F 30/20* (2020.01); *G01N 2001/4038* (2013.01); *G06F 2111/10* (2020.01)

(58) Field of Classification Search
CPC ..... G01R 31/00; G06F 2111/10; G06F 30/20; Y10T 436/25; Y10T 436/255; Y10T 436/2575
USPC ........ 702/19, 22, 27, 32; 436/149, 150, 174, 436/178, 180; 422/82.01, 502, 527; 204/450, 451, 452
See application file for complete search history.

(56) References Cited

FOREIGN PATENT DOCUMENTS

| | | |
|---|---|---|
| KR | 10-15041090000 B | 3/2015 |
| KR | 1020160081379 | 7/2016 |
| WO | 2015/160996 A1 | 10/2015 |

OTHER PUBLICATIONS

Chen et al. Biomicrofluidics, vol. 10, Feb. 18, 2016, pp. 0141119-1-0141119-12.*
Chiu et al. Sensors, vol. 15, Dec. 5, 2015, pp. 30704-30715.*
Choi et al. BioChip J. vol. 14(1), Mar. 13, 2020, pp. 100-109.*
Sueyoshi et al. "On-Line Sample Preconcentration and Separation Technique Based on Transient Trapping in Microchip Micellar Electrokinetic Chromatography" Anal. Chem. 2008, 80, 1255-1262.
Milanova et al. "Electrophoretic mobility measurements of fluorescent dyes using on-chip capillary electrophoresis" Electrophoresis 2011, 32, 3286-3294.

* cited by examiner

METHOD FOR DETERMINING CONCENTRATED FORM OF ANALYTE AND METHOD FOR CONVERTING CONCENTRATED FORM OF ANALYTE

TECHNICAL FIELD

The present invention relates to a method of determining a preconcentration type of an analyte and a method of converting a preconcentration type of an analyte, and more particularly, to a method of determining a preconcentration type of an analyte, by which the preconcentration type of the analyte, e.g., particles or small particles in a material, may be previously determined, and a method of converting a preconcentration type of an analyte, by which the preconcentration type of the analyte is converted by adjusting a design parameter of a material preconcentration device.

BACKGROUND ART

To detect a target material such as a biomaterial, biodiesel, or heavy metal in a sample, a high-priced detector may be used or a concentration of the target material may be amplified in advance in a sample preparation step.

A variety of preconcentration methods are present and centrifugation is most commonly used for a cell-level material. However, based on centrifugation, a certain quantity of cells is destroyed due to a high rotational force in a separation process. The quantity of destroyed cells increases in proportion to the amount of a sample and thus a method of nondestructively preconcentrating a target material is required. For example, when destruction of red blood cells is reducible and a preconcentrated amount thereof is increasable, the amount of blood to be collected from a patient may be reduced and a precise biopsy may be enabled by minimizing pain of the patient.

DETAILED DESCRIPTION OF THE INVENTION

Technical Problem

A method of preconcentrating a material by using an ion concentration polarization (ICP) phenomenon has been academically reported. An equilibrium position of preconcentration of an analyte in a diffusion layer outside an ion depletion zone generated due to ICP may be determined based on advection caused by a flow and electro-migration caused by an electrophoretic mechanism.

A preconcentration type of the analyte may occur differently depending on whether advection or electro-migration is dominant in the whole diffusion layer. However, a quantitative correlation between an arbitrary application condition, e.g., a voltage, a flow rate, or an electrophoretic mobility of the analyte, and the preconcentration type of the analyte has not been obtained.

The present invention provides a method of determining a preconcentration type of an analyte, by which the preconcentration type of the analyte may be previously determined.

The present invention also provides a method of determining a preconcentration type of an analyte, by which a reference value for previously determining the preconcentration type of the analyte may be prepared and applied to design a material preconcentration device.

The present invention also provides a method of converting a preconcentration type of an analyte, by which the preconcentration type may be converted based on a design parameter of a material preconcentration device.

The present invention also provides a method of converting a preconcentration type of an analyte, by which a process type of a target material, e.g., high preconcentration or extraction, may be preset and a material preconcentration device may be designed to correspond to the process type.

However, the scope of the present invention is not limited thereto.

Technical Solution

According to an aspect of the present invention, there is provided a method of determining a preconcentration type of an analyte in a material preconcentration device, the method including (a) establishing a critical mobility model, (b) calculating a critical mobility by applying a parameter value to the critical mobility model, and (c) determining the preconcentration type of the analyte by comparing the calculated critical mobility to an absolute value of an electrophoretic mobility of the analyte.

In (a), the critical mobility model may be established as $$\mu_{cr} = \frac{\mu_+ + \mu_-}{\frac{I}{zFQc_0} - \frac{D_+ - D_-}{D_{eff}} \frac{\exp\left(-\frac{QL}{D_{eff}A}\right)}{1 - \exp\left(-\frac{QL}{D_{eff}A}\right)}}$$

(where $\mu_+$ and $\mu_-$ respectively denote electrophoretic mobilities of cations and anions, $D_+$ and $D_-$ respectively denote diffusion coefficients of cations and anions, $D_{eff}$ denotes a corrected diffusion coefficient, Q denotes a flow rate, A denotes a cross-sectional area of a main microchannel, L denotes a length of the main microchannel, $c_0$ denotes a bulk concentration, z denotes an ion valence of the analyte, and F denotes a Faraday constant).

In (b), the parameter value may be applied by substituting a designed condition of the material preconcentration device in the critical mobility model.

An equilibrium position of preconcentration of the analyte in the material preconcentration device may be determined as a sum of advection caused by a flow and electro-migration caused by an electrophoretic mechanism.

In (c), when the absolute value of the electrophoretic mobility of the analyte is less than the calculated critical mobility, a mechanism of advection may be dominant.

The preconcentration type of the analyte may be a type in which the analyte is stacked at a certain position.

In (c), when the absolute value of the electrophoretic mobility of the analyte is greater than the calculated critical mobility, a mechanism of electro-migration may be dominant.

The preconcentration type of the analyte may be a type in which the equilibrium position of preconcentration propagates.

The material preconcentration device may include a main microchannel having, at an end thereof, an inlet for supplying the analyte, and an ion-selective membrane provided on at least one surface of the main microchannel, and, when an electric field is applied to the material preconcentration device, an ion concentration polarization (ICP) phenomenon may occur in a part of the main microchannel adjacent to the ion-selective membrane and thus an ion depletion layer may be generated.

The ion-selective membrane may be made of Nafion ($C_7HF_{13}O_5S.C_2F_4$).

The main microchannel may have a dead-end channel structure, and the critical mobility of the material preconcentration device may be 0.

According to another aspect of the present invention, there is provided a method of converting a preconcentration type of an analyte in a material preconcentration device, the method including (a) establishing a critical mobility model, and (b) changing a design parameter of the material preconcentration device based on an absolute value of an electrophoretic mobility of the analyte, wherein a preconcentration type in which a mechanism of advection is dominant is achieved when a critical mobility calculated by applying the design parameter to the critical mobility model is greater than the absolute value of the electrophoretic mobility of the analyte, and a preconcentration type in which a mechanism of electro-migration is dominant is achieved when the calculated critical mobility is less than the absolute value of the electrophoretic mobility of the analyte.

The preconcentration type in which the mechanism of advection is dominant may be a type in which the analyte is stacked at a certain position, and the preconcentration type in which the mechanism of electro-migration is dominant may be a type in which an equilibrium position of preconcentration propagates.

Advantageous Effects

As described above, according to an embodiment of the present invention, a preconcentration type of an analyte may be previously determined.

According to an embodiment of the present invention, a reference value for previously determining a preconcentration type of an analyte may be prepared and applied to design a material preconcentration device.

According to an embodiment of the present invention, a preconcentration type may be converted based on a design parameter of a material preconcentration device.

According to an embodiment of the present invention, a process type of a target material, e.g., high preconcentration or extraction, may be preset and a material preconcentration device may be designed to correspond to the process type.

However, the scope of the present invention is not limited to the above-described effects.

MODE OF THE INVENTION

Figure 1:
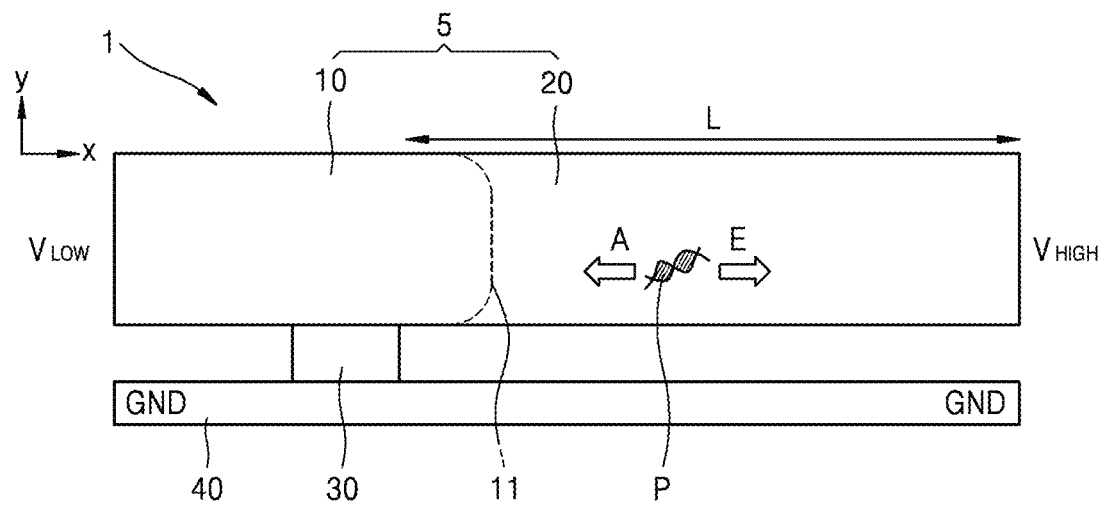
FIG. 1 is a schematic diagram of a material preconcentration device according to an embodiment of the present invention.

The following detailed descriptions of the invention will be made with reference to the accompanying drawings illustrating specific embodiments of the invention by way of example. These embodiments will be described in detail such that the invention can be carried out by one of ordinary skill in the art. It should be understood that various embodiments of the invention are different, but are not necessarily mutually exclusive. For example, a specific shape, structure, and characteristic of an embodiment described herein may be implemented in another embodiment without departing from the scope of the invention. In addition, it should be understood that a position or placement of each component in each disclosed embodiment may be changed without departing from the scope of the invention. Accordingly, there is no intent to limit the invention to the following detailed descriptions. The scope of the invention is defined by the appended claims and encompasses all equivalents that fall within the scope of the appended claims. In the drawings, like reference numerals denote like functions, and the dimensions such as lengths, areas, and thicknesses of elements may be exaggerated for clarity.

Hereinafter, to allow one of ordinary skill in the art to easily carry out the invention, embodiments of the present invention will be described in detail with reference to the accompanying drawings.

As used herein, the term "material" (or "sample") refers to a material including micro- or nano-sized small particles. Examples of the material may include blood, microalgae, and other fluids. In this case, examples of the small particles included in the material may include red blood cells and algae cells but are not limited thereto.

FIG. 1 is a schematic diagram of a material preconcentration device 1 according to an embodiment of the present invention.

Referring to FIG. 1, the material preconcentration device 1 of the present invention may include a main microchannel 5 including an ion depletion layer 10 and a diffusion layer 20, an ion-selective membrane 30, and a ground microchannel 40.

The main microchannel 5 may have, at an end and another end thereof, an inlet and an outlet through which an analyte P enters and exits. The main microchannel 5 may extend in a direction in such a manner that a material may easily move along a path.

The ion-selective membrane 30 may be provided on at least one surface (a lower surface) of the main microchannel 5. The ion-selective membrane 30 may be made of a porous nanomaterial such as Nafion. Alternatively, the ion-selective membrane 30 may include a material capable of transmitting cations or anions.

When an electric field $V_{HIGH}$ and $V_{LOW}$ is applied to the end and the other end of the main microchannel 5, an ion concentration polarization (ICP) phenomenon may occur in a part of the main microchannel 5 adjacent to the ion-selective membrane 30 and thus the ion depletion layer 10 may be generated. On the other hand, an ion enrichment layer (not shown) may be generated between the ion-selective membrane 30 and the ground microchannel 40.

The ICP phenomenon is one of electrochemical communication phenomena observed in the vicinity of a structure having a nanomembrane. It is theoretically known that, when the thickness of an electric double layer is similar to the size of a nanomembrane, the electric double layer overlaps in the nanomembrane and thus single ion permeability is shown. Ions having charges such as wall charges may not pass through the nanomembrane due to diffusion and drift force and only ions having charges opposite to the wall charges pass, and thus depletion and enrichment of ions occur at a boundary surface of the nanomembrane.

Using a property that the analyte P having the same polarity as the nanomembrane may not pass through the ion depletion layer 10, the ion depletion layer 10 may be utilized as a preconcentration mechanism of the analyte P. The analyte P may be preconcentrated in the diffusion layer 20 from a boundary 11 between the ion depletion layer 10 and the diffusion layer 20.

An equilibrium position of preconcentration of the analyte P may be determined based on advection A caused by a flow and electro-migration E caused by an electrophoretic mechanism, and a preconcentration type of the analyte P may differ depending on dominance of the advection A or the electro-migration E.

Specifically, the preconcentration type may be determined by comparing an absolute value of an electrophoretic mobility of the analyte P to a critical mobility. When the absolute value of the electrophoretic mobility of the analyte P is less than the critical mobility, a mechanism of the advection A may be dominant. When the absolute value of the electrophoretic mobility of the analyte P is greater than the critical mobility, a mechanism of the electro-migration E may be dominant. The analyte P having the absolute value of the electrophoretic mobility less than the critical mobility may be stacked at a specific position of the diffusion layer 20, and the analyte P having the absolute value of the electrophoretic mobility greater than the critical mobility may propagate in a reservoir direction (e.g., an inlet/outlet direction) by varying the equilibrium position of preconcentration in the diffusion layer 20.

To quantitatively obtain the above-described correlation, a method of determining a preconcentration type of the analyte P in the material preconcentration device 1, according to the present invention, includes (a) establishing a critical mobility model (S10), (b) calculating a critical mobility by applying a parameter value to the critical mobility model (S20), and (c) determining a preconcentration type of the analyte P by comparing the calculated critical mobility to an absolute value of an electrophoretic mobility of the analyte P (S30).

Initially, the critical mobility model is established (S10).

In FIG. 1, assuming (1) the fully-developed ion depletion layer 10, (2) a local electroneutral principle of the diffusion layer 20: a sum of charges generated by cations and anions of an electrolyte is 0, and (3) an extremely low concentration of the analyte P compared to a concentration of the electrolyte, a critical mobility in a z:z symmetric electrolyte (i.e., an electrolyte having equal ion valences of cations and anions, e.g., NaCl or KCl) is analytically obtained.

The critical mobility may be obtained based on an ionic flux balance of the analyte P as shown below.

$$j_A \approx \frac{z_A}{|z_A|}\mu_A c_A E_x - c_A u_x \quad \text{(Formula 1)}$$

Herein, $z_A$ denotes an ion valence of the analyte P, $\mu_A$ denotes an absolute value of an electrophoretic mobility of the analyte P, $c_A$ denotes a local concentration of the analyte P, $E_x$ denotes an x-direction electric field in the diffusion layer 20, and $u_x$ denotes an x-direction flow velocity in the diffusion layer 20. The first term of a right-hand side refers to electro-migration flux of the analyte P and the second term refers to advection flux of the analyte P.

Analytical solutions of the electric field $E_x$ and the flow velocity $u_x$ in the diffusion layer 20 are required to analytically express ionic flux of the analyte P, and thus this step is performed in advance.

(Analytical expressions of the electric field $E_x$ and the flow velocity $u_x$ in the diffusion layer 20)

Ionic fluxes of cations and anions of the z:z symmetric electrolyte are as shown below.

$$j_+ = -D_+ \frac{dc_+}{dx} + \mu_+ c_+ E_x - c_+ u_x \quad \text{(Formula 2)}$$

$$j_- = -D_- \frac{dc_-}{dx} - \mu_- c_- E_x - c_- u_x \quad \text{(Formula 3)}$$

Herein, $j_+$ and $j_-$ respectively denote ionic fluxes of cations and anions, $D_+$ and $D_-$ respectively denote diffusion coefficients of cations and anions, $c_+$ and $c_-$ respectively denote local concentrations of cations and anions, and $\mu_+$ and $\mu_-$ respectively denote electrophoretic mobilities of cations and anions. $\mu_+$ and $\mu_-$ are set to have positive values for convenience of explanation, and a direction of movement due to a given electric field is indicated by a sign in front of the electrophoretic mobility.

The laws of conservation of mass for cations and anions may be expressed as differential equations as shown below.

$$\frac{\partial c_+}{\partial t} + \frac{\partial j_+}{\partial x} = 0 \quad \text{(Formula 4)}$$

$$\frac{\partial c_-}{\partial t} + \frac{\partial j_-}{\partial x} = 0 \quad \text{(Formula 5)}$$

(Formula 4) and (Formula 5) may be simplified on the assumptions described below.

(1) The fully-developed ion depletion layer 10

$$\frac{\partial c_+}{\partial t} = 0 \quad \text{(Formula 6)}$$

$$\frac{\partial C_-}{\partial t} = 0 \quad \text{(Formula 7)}$$

(2) The local electroneutral principle of the diffusion layer 20

$$zc_+ - zc_- + z_A c_A = 0 \quad \text{(Formula 8)}$$

(3) The extremely low concentration of the analyte P $$c_A \ll c_+, c_- \quad \text{(Formula 9)}$$

Based on the assumptions (2) and (3), $$c_+ = c_- \equiv c \quad \text{(Formula 10)}$$

may be defined.

Using the assumption (1), based on $$\frac{\partial j_+}{\partial x} = 0 \text{ and} \qquad \text{(Formula 11)}$$

$$\frac{\partial j_-}{\partial x} = 0, \qquad \text{(Formula 12)}$$

(Formula 4) and (Formula 5) may be modified into an equation shown below based on the definitions of ionic fluxes.

$$\frac{d}{dx}\left(\frac{j_+}{\mu_+} + \frac{j_-}{\mu_-}\right) = \frac{d}{dx}\left[-\left(\frac{D_+}{\mu_+} + \frac{D_-}{\mu_-}\right)\frac{dc}{dx} - \left(\frac{1}{\mu_+} + \frac{1}{\mu_-}\right)cu_x\right] = 0 \qquad \text{(Formula 13)}$$

A boundary condition for (Formula 11) and (Formula 12) is (c=0, in x=L*), (c=c_0, in x=L). Herein, L* denotes a length of the ion depletion layer 10, L denotes a length of the main microchannel 5, and $c_0$ denotes a bulk concentration.

Therefore, the concentration of the electrolyte in the diffusion layer 20 may be expressed as an analytical solution shown below.

$$c(x) = c_0 \frac{1 - \exp\left[-\frac{Q}{D_{eff}A}(x - L^*)\right]}{1 - \exp\left[-\frac{Q}{D_{eff}A}(L - L^*)\right]} \qquad \text{(Formula 14)}$$

Herein, $D_{eff}$ denotes a corrected diffusion coefficient $$\left(D_{eff} \equiv \left(\frac{D_+}{\mu_+} + \frac{D_-}{\mu_-}\right)\frac{\mu_+\mu_-}{\mu_+ + \mu_-}\right),$$

Q denotes a flow rate, A denotes a cross-sectional area of the main microchannel 5, and $Q=u_xA$ is satisfied in relation to the flow velocity $u_x$.

An ion current density i is defined as shown below.

$$i = zF(j_+ - j_-) \qquad \text{(Formula 15)}$$

(where z denotes an ion valence of the analyte P, and F denotes a Faraday constant.)

In the coordinate system of FIG. 1, a relationship between an ion current I and the ion current density i is as shown below.

$$I = -iA \qquad \text{(Formula 16)}$$

Thus, the ion current I may be expressed as an analytical solution of concentration as shown in (Formula 14).

$$I = zAF\left[(D_+ - D_-)\frac{dc}{dx} - (\mu_+ + \mu_-)cE_x\right] \qquad \text{(Formula 17)}$$

Therefore, the electric field in the diffusion layer 20 may be analytically expressed as shown below.

$$E_x = \frac{D_+ - D_-}{\mu_+ + \mu_-}\frac{1}{c}\frac{dc}{dx} - \frac{I}{zFA(\mu_+ + \mu_-)c} \qquad \text{(Formula 18)}$$

(Induction of a Critical Mobility)

When the flux of the analyte P satisfies (Formula 1)=0 at the inlet of the main microchannel 5, this means that the advection A is balanced with the electro-migration E and a preconcentration position occurs at the inlet of the main microchannel 5. Such a situation is assumed to be a critical situation. The electrophoretic mobility $\mu_A$ of the analyte P in the critical situation is defined as a critical mobility $\mu_{cr}$.

In the material preconcentration device 1 using the ion-selective membrane 30, the ion valence of the preconcentrated analyte P satisfies zA<0 and thus zA/|zA|=−1 is satisfied. When analytical solutions of an electric field and a flow field [(Formula 18)] is substituted in the flux of the analyte P [(Formula 1)], the critical mobility $\mu_{cr}$ may be expressed as shown below.

$$\mu_{cr} = \frac{\mu_+ + \mu_-}{\frac{I}{zFQc_0} - \frac{D_+ - D_-}{D_{eff}}\frac{\exp\left(-\frac{Q}{D_{eff}A}(L - L^*)\right)}{1 - \exp\left(-\frac{Q}{D_{eff}A}(L - L^*)\right)}} \qquad \text{(Formula 19)}$$

In general, the length of the main microchannel 5 is much greater than the length of the ion depletion layer 10 (L*<<L) and thus the critical mobility $\mu_{cr}$ may be approximated as shown below.

$$\mu_{cr} = \frac{\mu_+ + \mu_-}{\frac{I}{zFQc_0} - \frac{D_+ - D_-}{D_{eff}}\frac{\exp\left(-\frac{QL}{D_{eff}A}\right)}{1 - \exp\left(-\frac{QL}{D_{eff}A}\right)}} \qquad \text{(Formula 20)}$$

(Formula 20) is a mathematical expression of an ultimately proposed critical mobility.

Then, the preconcentration type of the analyte P is determined by comparing the critical mobility per calculated by applying a parameter value to the critical mobility model, to the absolute value of the electrophoretic mobility of the analyte P (S20).

The flow rate Q, the cross-sectional area A of the main microchannel 5, the ion current I, the bulk concentration $c_0$, the length L of the main microchannel 5, etc. in (Formula 20) are conditions arbitrarily changeable to design values of the material preconcentration device 1. Therefore, when the material preconcentration device 1 is designed, the critical mobility $\mu_{cr}$ may be calculated using (Formula 20). That is, the application of a parameter value to the critical mobility model may be understood as determination of an arbitrary application condition such as a voltage, a flow rate, an electrophoretic mobility of an analyte by designing the material preconcentration device 1.

Then, the preconcentration type of the analyte P is determined by comparing the calculated critical mobility $\mu_{cr}$ to the absolute value of the electrophoretic mobility $\mu_A$ of the analyte P (S30). The preconcentration type is divided into a stacking type and a propagating type.

Figure 2A:
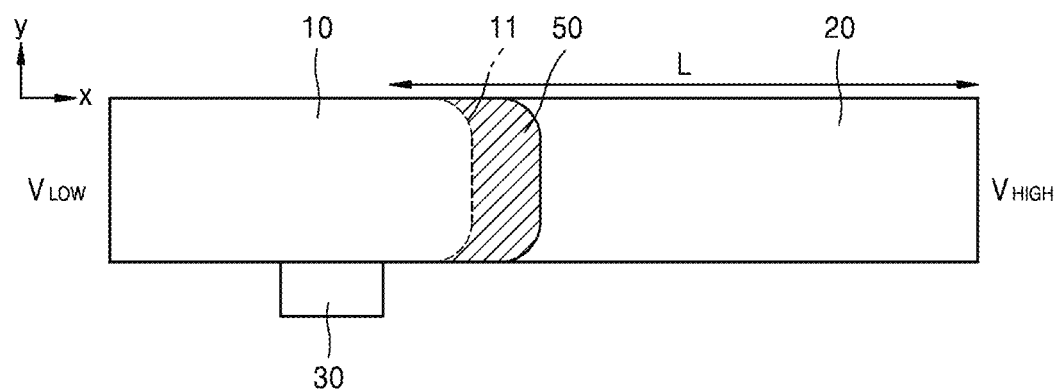
FIGS. 2A and 2B illustrate schematic diagrams showing a case in which a mechanism of advection is dominant in a diffusion layer, according to an embodiment of the present invention.
Figure 2B:
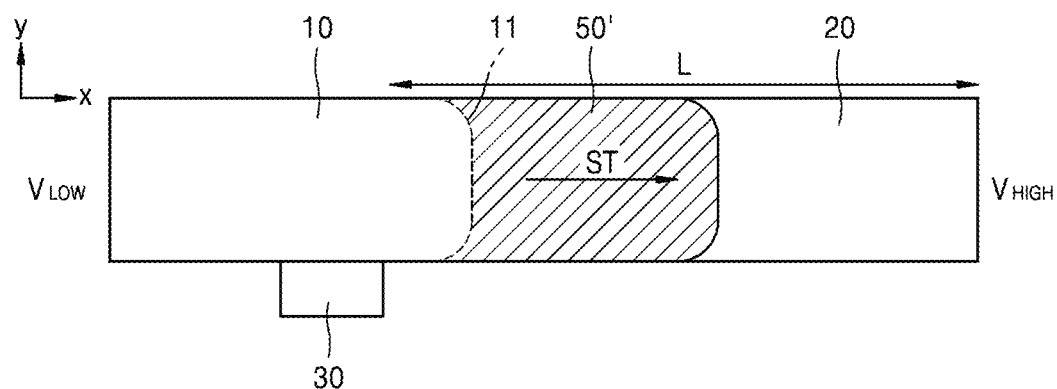
Figure 3A:
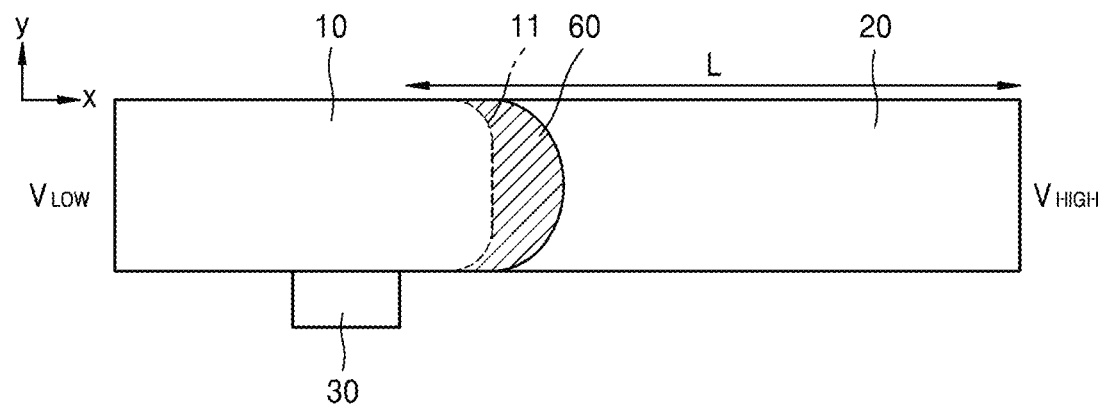
FIGS. 3A and 3B illustrate schematic diagrams showing a case in which a mechanism of electro-migration is dominant in a diffusion layer, according to an embodiment of the present invention.
Figure 3B:
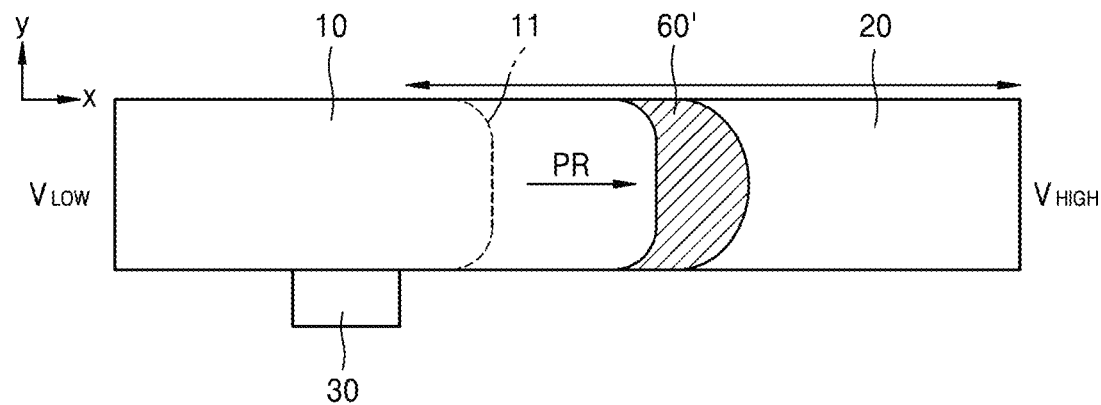

FIG. 2 illustrates schematic diagrams showing a case in which the mechanism of the advection A is dominant in the diffusion layer 20, according to an embodiment of the present invention. FIG. 3 illustrates schematic diagrams showing a case in which the mechanism of the electro-migration E is dominant in the diffusion layer 20, according to an embodiment of the present invention.

Referring to FIG. 2, when the absolute value of the electrophoretic mobility of the analyte P is less that the critical mobility ($\mu_A < \mu_{cr}$), the mechanism of the advection A may be dominant. As shown in (a) of FIG. 2, the analyte P may be preconcentrated (see reference numeral 50) at a specific position from a boundary 11 between the ion depletion layer 10 and the diffusion layer 20. As shown in (b) of FIG. 2, when preconcentration is continued, an equilibrium position of preconcentration may be stacked (see reference symbol ST) and a preconcentrated amount of the analyte P may increase (50→50').

Referring to FIG. 3, when the absolute value of the electrophoretic mobility of the analyte P is greater than the critical mobility ($\mu_A > \mu_{cr}$), the mechanism of the electromigration E may be dominant. As shown in (a) of FIG. 3, the analyte P may be preconcentrated (see reference numeral 60) at a specific position from the boundary 11 between the ion depletion layer 10 and the diffusion layer 20. As shown in (b) of FIG. 3, when preconcentration is continued, an equilibrium position of preconcentration may propagate (see reference symbol PR) in a reservoir direction (e.g., an inlet/outlet direction) and a preconcentrated amount of the analyte P may increase (60→60').

Figure 4A:
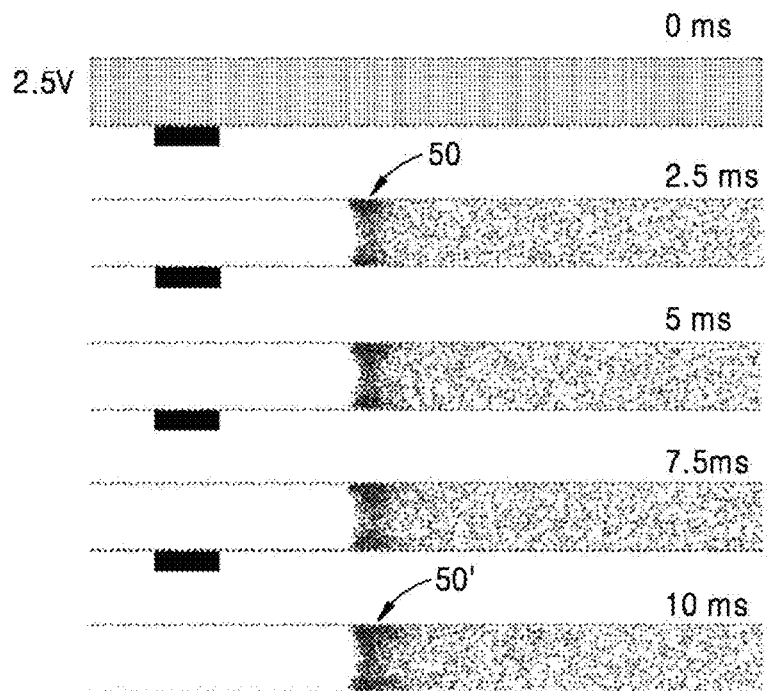
FIGS. 4A and 4B illustrate schematic diagrams showing Langevin dynamics simulation results of particles having absolute values of electrophoretic mobilities corresponding to 90% and 110% of a critical mobility, according to an experimental example of the present invention.
Figure 4B:
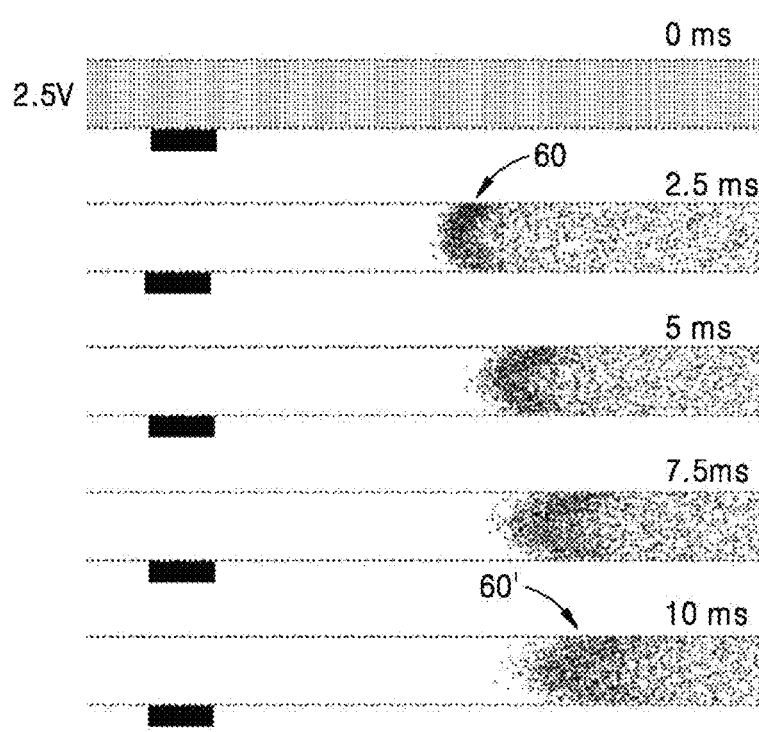

FIG. 4 illustrates schematic diagrams showing Langevin dynamics simulation results of particles having absolute values of electrophoretic mobilities corresponding to 90% and 110% of a critical mobility, according to an experimental example of the present invention.

As an embodiment for numerical verification of a critical mobility, the main microchannel 5 having a length of $1 \times 10^{-5}$ m from the cation-selective membrane 30 to a reservoir (e.g., an inlet/outlet), a depth of 1 μm, and a width of 1 μm is used. By applying asymmetrical voltages of 2.5 V and 5 V to both ends of the main microchannel 5, an ion current of $4.19 \times 10^{-5}$ A flows and a flow rate of $2.11 \times 10^{-10}$ m$^3$/s is induced. A critical mobility $\mu_{cr}$ of $1.88 \times 10^{-8}$ m$^2$ V$^{-1}$ s$^{-1}$ is obtained using the material preconcentration device 1 configured as described above.

(a) of FIG. 4 shows a result of particles P having an absolute value of an electrophoretic mobility $\mu_A$ corresponding to 90% of the critical mobility $\mu_{cr}$, and (b) of FIG. 4 shows a result of particles P having an absolute value of an electrophoretic mobility $\mu_A$ corresponding to 110% of the critical mobility $\mu_{cr}$. As described above, (a) of FIG. 4 shows that, when preconcentration is continued as time passes, an equilibrium position of preconcentration is stacked (see reference symbol ST) and a preconcentrated amount of the analyte P increases (50→50'). (b) of FIG. 4 shows that, when preconcentration is continued, an equilibrium position of preconcentration propagates (see reference symbol PR) in a reservoir direction (e.g., an inlet/outlet direction) and a preconcentrated amount of the analyte P increases (60→60').

Figure 5A:
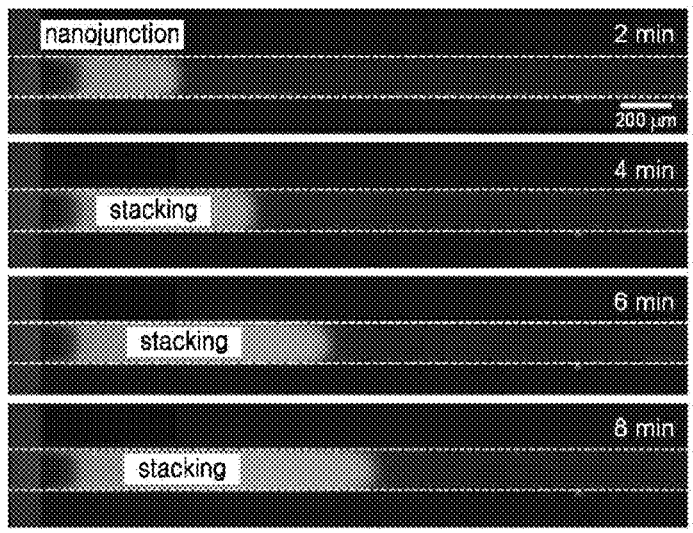
FIGS. 5A and 5B illustrate microscopic images showing preconcentration types of materials, according to an experimental example of the present invention.
Figure 5B:
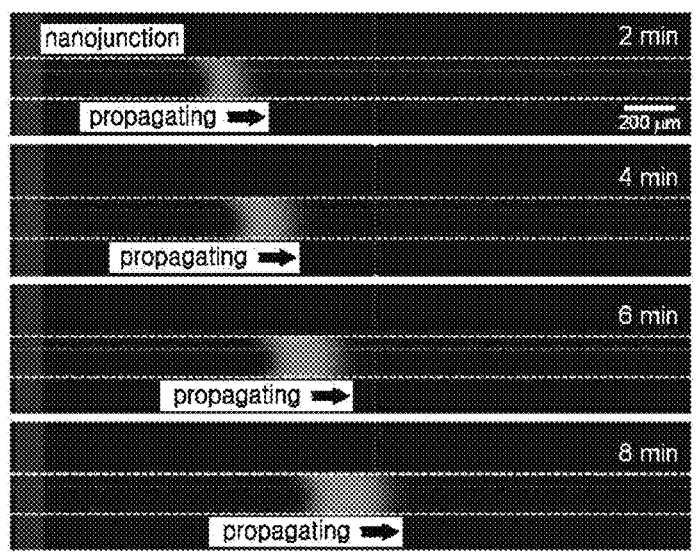

FIG. 5 illustrates microscopic images showing preconcentration types of materials, according to an experimental example of the present invention.

As an embodiment for experimental verification of a critical mobility, the main microchannel 5 having a length of $7 \times 10^{-3}$ m from the cation-selective membrane 30 to a reservoir (e.g., an inlet/outlet), a depth of 15 μm, and a width of 200 μm is used. By applying asymmetrical voltages of 15 V and 30 V to both ends of the main microchannel 5, an ion current of $1.01 \times 10^{-8}$ A flows and a flow rate of $2.29 \times 10^{-14}$ m$^3$/s is induced. A critical mobility $\mu_{cr}$ of $2.7 \times 10^{-8}$ m$^2$ V$^{-1}$ s$^{-1}$ is obtained using the material preconcentration device 1 configured as described above.

(a) of FIG. 5 shows a preconcentration type of sulforhodamine B dye molecules having an absolute value of an electrophoretic mobility of $1.3 \times 10^{-8}$ m$^2$ V$^{-1}$ s$^{-1}$, and (b) of FIG. 5 shows a preconcentration type of Alexa 488 dye molecules having an absolute value of an electrophoretic mobility of $3.6 \times 10^{-8}$ m$^2$ V$^{-1}$ s$^{-1}$. Stacking preconcentration occurs in (a) of FIG. 5 in which the absolute value of the electrophoretic mobility is less than the critical mobility $\mu_{cr}$ of $2.7 \times 10^{-8}$ m$^2$V$^{-1}$ s$^{-1}$, and propagating preconcentration occurs in (b) of FIG. 5 in which the absolute value of the electrophoretic mobility is greater than the critical mobility $\mu_{cr}$ of $2.7 \times 10^{-8}$ m$^2$ V$^{-1}$ s$^{-1}$. As such, it is shown that the obtained critical mobility is usable as a reference value for determining a preconcentration type.

Figure 6A:
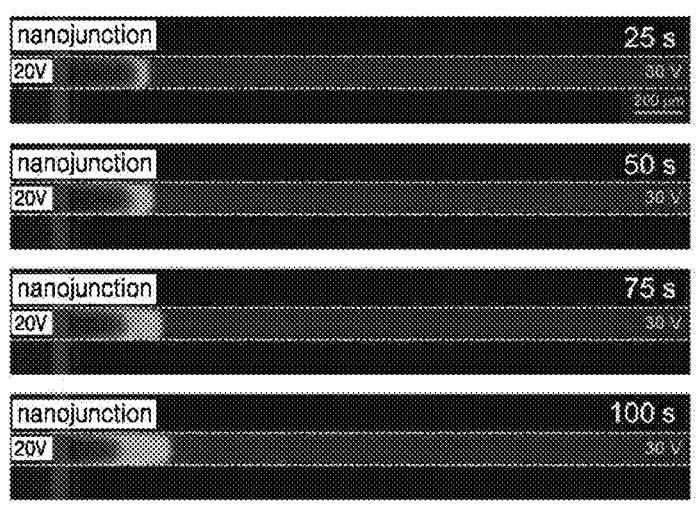
FIGS. 6A and 6B illustrate microscopic images showing preconcentration types using a critical mobility, according to another experimental example of the present invention.
Figure 6B:
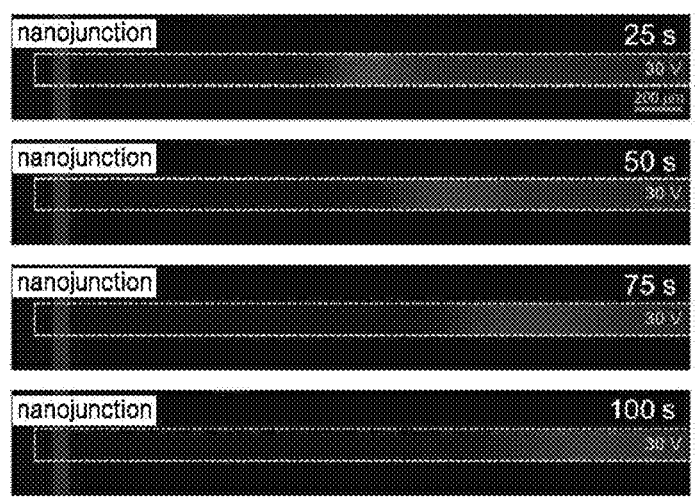

FIG. 6 illustrates microscopic images showing preconcentration types using a critical mobility, according to another experimental example of the present invention.

The main microchannel 5 having a length of $7 \times 10^{-3}$ m from the cation-selective membrane 30 to a reservoir (e.g., an inlet/outlet), a depth of 15 μm, and a width of 200 μm is used. By applying asymmetrical voltages of 15 V and 30 V to both ends of the main microchannel 5, an ion current of $1.01 \times 10^{-8}$ A flows and a flow rate of $2.29 \times 10^{-14}$ m$^3$/s is induced. A critical mobility $\mu_{cr}$ of $2.7 \times 10^{-8}$ m$^2$ V$^{-1}$ s$^{-1}$ is obtained using the material preconcentration device 1 configured as described above.

(a) of FIG. 6 shows a preconcentration type of sulforhodamine B dye molecules having an absolute value of an electrophoretic mobility of $1.3 \times 10^{-8}$ m$^2$ V$^{-1}$ s$^{-1}$, and stacking preconcentration occurs at a specific position.

In (b) of FIG. 6, the material preconcentration device 1 designed in a dead-end channel structure is used. The dead-end channel structure may be implemented by supplying air to or closing an inlet/outlet. Since a path to a reservoir (e.g., the inlet/outlet) is blocked, the flow rate Q is 0. When Q=0 is substituted in (Formula 20), the critical mobility $\mu_{cr}$ is 0 regardless of the ion current i. Therefore, since sulforhodamine B dye molecules has an absolute value of an electrophoretic mobility greater than the critical mobility, it is predicted that propagating preconcentration will occur. After an experiment, the predicted result is actually shown in (b) of FIG. 6. Furthermore, since propagating preconcentration may be predicted in the dead-end channel structure regardless of the electrophoretic mobility, the dead-end channel structure may be directly used when propagating preconcentration is desired.

As such, it is shown that, even then the same analyte is used, different preconcentration types may be obtained by changing an operating condition and a design value of the material preconcentration device 1.

As described above, according to the present invention, a preconcentration type of an analyte may be previously determined by applying a parameter value to a critical mobility model. Examples of the parameter value include electrophoretic mobilities $\mu_+$ and $\mu_-$ and ionic fluxes $D_+$ and $D_-$ of cations and anions an electrolyte, an ion current I, a flow rate Q, and a bulk concentration $c_0$ of the electrolyte, and serve as design values and operating conditions of the material preconcentration device 1. By substituting the parameter value in the critical mobility model, it may be previously determined whether a preconcentration type is converted. Therefore, a preconcentration type of an analyte may be converted without any structural design change by changing an operating condition of the material preconcentration device 1 using the ion depletion layer 10. For example, a condition for stacking preconcentration may be set to highly condense a material, and a condition for propagating preconcentration may be set to extract a preconcentrated material.

By changing a design parameter value of the material preconcentration device 1 based on an induced critical mobility, a preconcentration type may be converted from a stacking type to a propagating type, or from a propagating type to a stacking type.

While the present invention has been particularly shown and described with reference to embodiments thereof, it will be understood by one of ordinary skill in the art that various changes in form and details may be made therein without departing from the scope of the present invention as defined by the following claims.

The invention claimed is:

1. A method of determining whether a preconcentrated analyte is stacked at a certain position in a material preconcentration device, the method comprising:
    (a) establishing a critical mobility model that determines whether a mechanism for advection or electro-migration is dominant during preconcentration of the analyte in the device based on a comparison of an absolute value of an electrophoretic mobility of the analyte with a critical mobility of the analyte;
    (b) calculating a critical mobility of the analyte by applying a parameter value to the critical mobility model, wherein the parameter value comprises an operating condition of the material preconcentration device; and
    (c) inputting an analyte to the material preconcentration device; and
    (d) operating the material preconcentration device to preconcentrate the analyte; and
    (e) determining that the preconcentrated analyte is stacked at a certain position in the device when the critical mobility calculated in step (b) is greater than the absolute value of the electrophoretic mobility of the analyte.

2. The method of claim 1, wherein, in step (a), the critical mobility model is established as $$\mu_{cr} = \frac{\mu_+ + \mu_-}{\frac{I}{zFQc_0} - \frac{D_+ - D_-}{D_{eff}} \cdot \frac{\exp\left(-\frac{QL}{D_{eff}A}\right)}{1 - \exp\left(-\frac{QL}{D_{eff}A}\right)}}$$

(where $\mu_+$ and $\mu_-$ respectively denote electrophoretic mobilities of cations and anions of an electrolyte, $D_+$ and $D_-$ respectively denote diffusion coefficients of cations and anions, $D_{eff}$ denotes a corrected diffusion coefficient of an electrolyte, Q denotes a flow rate of solution entering a main microchannel of the material preconcentration device, I denotes an ion current, A denotes a cross-sectional area of the main microchannel of the material preconcentration device, L denotes a length of the main microchannel, $c_0$ denotes a bulk concentration of the electrolyte, z denotes an ion valence of the analyte, and F denotes a Faraday constant).

3. The method of claim 2, wherein, in step (b), the parameter value is applied by substituting an operating condition of the material preconcentration device in the critical mobility model.

4. The method of claim 3, wherein the parameter value includes:
    a flow rate Q of solution entering the main microchannel of the material preconcentration device,
    an ion current I,
    a cross sectional area A of the main microchannel of the material preconcentration device, and
    a length L of the main microchannel.

5. The method of claim 1, wherein an equilibrium position of preconcentration of the analyte in the material preconcentration device is determined as a sum of advection caused by a flow of the analyte and electro-migration of the analyte caused by an electrophoretic mechanism, wherein the equilibrium position of the preconcentration of the analyte propagates in an inlet/outlet direction during preconcentration.

6. The method of claim 1, wherein the material preconcentration device comprises a main microchannel having an inlet at one end for supplying the analyte thereto, and an ion selective membrane provided on at least one surface of the main microchannel, and
    wherein, when an electric field is applied to the material preconcentration device, an ion concentration polarization (ICP) phenomenon occurs in a part of the main microchannel adjacent to the ion selective membrane which causes an ion depletion layer to be generated.

7. The method of claim 6, wherein the ion-selective membrane is made of $C_7HF_{13}O_5S \cdot C_2F_4$.

8. A method of determining whether an equilibrium position of preconcentration of an analyte to be preconcentrated in a material preconcentration device propagates in the device, the method comprising:
    (a) establishing a critical mobility model that determines whether a mechanism for advection or electro-migration is dominant during preconcentration of the analyte based on a comparison of an absolute value of an electrophoretic mobility of the analyte with a critical mobility of the analyte;
    (b) calculating a critical mobility of the analyte by applying a parameter value to the critical mobility model, wherein the parameter value comprises an operating condition of the material preconcentration device;
    (c) inputting an analyte to the material preconcentration device;
    (d) operating the material preconcentration device to preconcentrate the analyte; and
    (e) determining that an equilibrium position of preconcentration of the preconcentrated analyte propagates in the device when the critical mobility calculated in step (b) is less than the absolute value of the electrophoretic mobility of the analyte.

9. The method of claim 8, wherein, in step (a), the critical mobility model is established as $$\mu_{cr} = \frac{\mu_+ + \mu_-}{\frac{I}{zFQc_0} - \frac{D_+ - D_-}{D_{eff}} \cdot \frac{\exp\left(-\frac{QL}{D_{eff}A}\right)}{1 - \exp\left(-\frac{QL}{D_{eff}A}\right)}}$$

(where $\mu+$ and $\mu-$ respectively denote electrophoretic mobilities of cations and anions of an electrolyte, D+ and D− respectively denote diffusion coefficients of cations and anions, Deff denotes a corrected diffusion coefficient of an electrolyte, Q denotes a flow rate of solution entering) a main microchannel of the material preconcentration device, I denotes an ion current, A denotes a cross-sectional area of the main microchannel of the material preconcentration device, L denotes a length of the main microchannel, $c_o$ denotes a bulk concentration of the electrolyte, z denotes an ion valence of the analyte, and F denotes a Faraday constant).

10. The method of claim 9, wherein, in step (b), the parameter value is applied by substituting an operating condition of the material preconcentration device in the critical mobility model.

11. The method of claim 10, wherein the parameter value includes:
a flow rate Q of solution entering the main microchannel of the material preconcentration device,
an ion current I,
a cross-sectional area A of the main microchannel of the material preconcentration device, and
a length L of the main microchannel.

12. The method of claim 8, wherein the equilibrium position of preconcentration of the analyte in the material preconcentration device is determined as a sum of advection caused by a flow of the analyte and electro-migration of the analyte caused by an electrophoretic mechanism, wherein the equilibrium position of the preconcentration of the analyte propagates in an inlet/outlet direction during pre-concentration.

13. The method of claim 8, wherein the material preconcentration device comprises a main microchannel having an inlet at one end for supplying the analyte thereto, and an ion-selective membrane provided on at least one surface of the main microchannel, and
wherein, when an electric field is applied to the material preconcentration device, an ion concentration polarization (ICP) phenomenon occurs in a part of the main microchannel adjacent to the ion-selective membrane which causes an ion depletion layer to be generated.

14. The method of claim 13, wherein the ion-selective membrane is made of $C_7HF_{13}O_5S.C_2F_4$.

* * * * *